(12) United States Patent
Imran

(10) Patent No.: US 9,144,586 B2
(45) Date of Patent: *Sep. 29, 2015

(54) METHOD FOR TREATING GLUCOSE RELATED DISORDERS USING STEM CELL-DERIVED GASTRO-INTESTINAL CELLS

(75) Inventor: Mir Imran, Los Altos Hills, CA (US)

(73) Assignee: INCUBE LABS, LLC, San Jose, CA (US)

( * ) Notice: Subject to any disclaimer, the term of this patent is extended or adjusted under 35 U.S.C. 154(b) by 741 days.

This patent is subject to a terminal disclaimer.

(21) Appl. No.: 13/066,247

(22) Filed: Apr. 7, 2011

(65) Prior Publication Data

US 2011/0286974 A1 Nov. 24, 2011

Related U.S. Application Data

(60) Provisional application No. 61/342,029, filed on Apr. 7, 2010.

(51) Int. Cl.
| | | |
|---|---|---|
| C12N 5/077 | (2010.01) | |
| A61K 35/38 | (2015.01) | |
| C12N 5/071 | (2010.01) | |

(52) U.S. Cl.
CPC .............. *A61K 35/38* (2013.01); *C12N 5/0679* (2013.01); *C12N 2502/1358* (2013.01); *C12N 2502/23* (2013.01); *C12N 2506/1346* (2013.01); *C12N 2506/1353* (2013.01)

(58) Field of Classification Search
CPC ....... A61K 35/545; A61K 35/12; C12N 5/06; C12N 5/0603; C12N 5/0606; C12N 5/0679; C12N 2502/03; C12N 2506/02; C12N 2506/025; C12N 2506/1346; C12N 2506/1353; C12N 2506/1361; C12N 2506/1369; C12N 2506/1376; C12N 2506/1384; C12N 2506/1392; C12N 2506/21
See application file for complete search history.

(56) References Cited

U.S. PATENT DOCUMENTS

| | | | | |
|---|---|---|---|---|
| 8,067,359 B2* | 11/2011 | Hayes et al. | ................ | 514/1.1 |
| 8,318,154 B2* | 11/2012 | Frost et al. | ................ | 424/94.5 |
| 8,367,708 B2* | 2/2013 | Hashimoto et al. | ........... | 514/374 |
| 8,470,885 B2* | 6/2013 | Szewczyk | ................ | 514/563 |
| 8,628,959 B2 | 1/2014 | Imran | | |
| 2006/0171992 A1* | 8/2006 | Gerhardt et al. | .............. | 424/439 |
| 2011/0002964 A1 | 1/2011 | Imran | | |
| 2014/0193462 A1 | 7/2014 | Imran | | |

FOREIGN PATENT DOCUMENTS

| | | |
|---|---|---|
| WO | WO 03016507 A2 | 2/2003 |
| WO | WO 03086373 A2 | 10/2003 |
| WO | WO 2005/003320 A2 | 1/2005 |

OTHER PUBLICATIONS

Dirks, "Brain Tumor Stem Cells: Bringing Order to the Chaos of Brain Cancer," *Journal of Clinical Oncology*, vol. 26 No. 17 (Jun. 10, 2008).
Ferrand, et al., "Human Bone Marrow-Derived Stem Cells Acquire Epithelial Characteristics through Fusion with Gastrointestinal Epithelial Cells" *PloS ONE*, May 2011, vol. 6 Issue 5, e19569, pp. 1-11.
Kolf, et al., "Biology of adult mesenchymal stem cells: regulation of niche, self-renewal and differentiation," *Arthritis Research & Therapy*, vol. 9 No. 1, available online http://arthritis-research.com/content/9/1/204 (Feb. 19, 2007).
U.S. Appl. No. 12/800,925 Advisory Action mailed Jul. 30, 2013.
U.S. Appl. No. 12/800,925 Final Office Action mailed Apr. 17, 2013.
U.S. Appl. No. 12/800,925 Non-Final Office Action mailed Jul. 18, 2012.
U.S. Appl. No. 12/800,925 Notice of Allowance mailed Sep. 27, 2014.

\* cited by examiner

*Primary Examiner* — Allison Fox
(74) *Attorney, Agent, or Firm* — Alston & Bird LLP

(57) ABSTRACT

Various embodiments of the invention provide methods of treating diabetes and other glucose regulation disorders. In one embodiment, the method comprises removing L-cells from a donor, obtaining stem cells from a patient, and culturing the L-cells in the presence of the stem cells under conditions such that the stem cells differentiate into stem cell-derived L-cells (SCDLC). An amount of the SCDLC is introduced into the patient sufficient to cause a lowering of the patient's blood glucose level after ingestion of food. In another embodiment, the method comprises removing K-cells from a donor, obtaining stem cells from a patient, and culturing the K-cells in the presence of the stem cells under conditions such that the stem cells differentiate into stem cell-derived K-cells (SCDKC). An amount of the SCDKC is introduced into the patient sufficient to cause a lowering of the patient's blood glucose level after ingestion of food.

29 Claims, No Drawings

METHOD FOR TREATING GLUCOSE RELATED DISORDERS USING STEM CELL-DERIVED GASTRO-INTESTINAL CELLS

RELATED APPLICATIONS

This application claims the benefit of priority to Provisional U.S. Patent Application No. 61/342,029, entitled "METHOD FOR TREATING DIABETES AND OTHER GLUCOSE REGULATION DISORDERS USING STEM CELLS", filed Apr. 7, 2010; the aforementioned priority application being hereby incorporated by reference for all purposes.

FIELD OF THE INVENTION

Embodiments of the present invention relate to the use of stem cells for the treatment of disorders. More specifically embodiments of the invention relate to the use of stem cells for the treatment of diabetes and other glucose regulation disorders.

BACKGROUND OF THE INVENTION

There are a number of disorders or conditions known as glucose regulation disorders in which the body is not able to regulate blood glucose within normal levels. Diabetes is one such disorder. Diabetes is a condition in which a person has a high blood glucose level as a result of their body either not producing enough insulin or because the cells of the body do not properly respond to insulin. The most common types of diabetes are: 1) Type 1 diabetes, which results from the body's failure to produce insulin; 2) Type 2 diabetes, which results from the body's resistance to insulin; and 3) gestational diabetes, in which pregnant women who have never had diabetes before, have a high blood glucose level during pregnancy.

Diabetes is a significant global health issue, with at least 171 million people worldwide suffering from the disease, about 2.8% of the population. The most common form of diabetes is Type 2 diabetes, which affects 90 to 95% of the U.S. diabetic population. Diabetes is typically treated through lifestyle modifications such as consuming an appropriate diabetic diet and exercising more, and through medications such as insulin. In spite of advances in treatment, there still remains a need for more efficacious treatment regimens for diabetes.

In the past 15 years, many discoveries have been made in understanding stem cells. There have been proposals to use stem cells for treating a wide variety of afflictions, including Parkinson's disease, spinal cord injuries, amyotrophic lateral sclerosis, and multiple sclerosis. Described herein are novel methods for the use of stem cells for the treatment of diabetes and other glucose regulation disorders.

SUMMARY OF THE INVENTION

Embodiments of the invention provide methods for treating diabetes and other glucose regulation disorders. Many embodiments involve the use of stem cells which are induced to differentiate into mimics of a patient's L-cells or K-cells, such that a release of incretins from the differentiated stem cells results in the lowering of the patient's blood glucose level and improved control of the patient's blood glucose levels. In one embodiment, the method comprises removing L-cells from a donor, obtaining stem cells from a patient, and culturing the L-cells in the presence of the stem cells under conditions such that the stem cells differentiate into stem cell-derived L-cells (SCDLC). An amount of the SCDLC is introduced into the patient sufficient to cause improved control of the patient's blood glucose including lowering of the patient's blood glucose levels following ingestion of a meal to normal blood glucose levels (also referred to herein as euglycemic levels). In another embodiment, the method comprises removing K-cells from a donor, obtaining stem cells from a patient, and culturing the K-cells in the presence of the stem cells under conditions such that the stem cells differentiate into stem cell-derived K-cells (SCDKC). An amount of the SCDKC is introduced into the patient sufficient to cause improved control of the patient's blood glucose including lowering of the patient's blood glucose levels following ingestion of a meal to euglycemic levels.

Further details of these and other embodiments and aspects of the invention are described more fully below.

DESCRIPTION OF PREFERRED EMBODIMENTS

There are a variety of gastro-intestinal hormones used for the regulation of glucose levels in the body. Among these hormones are insulin, glucagon and incretins. Insulin is produced by the beta cells of the islets of Langerhans of the pancreas. Insulin triggers cells to take up glucose, thereby reducing the level of glucose in the blood. Glucagon is produced by the alpha cells of the islets of Langerhans of the pancreases. Glucagon has the opposite effect of insulin on blood glucose levels, i.e., glucagon stimulates the release of glucose by liver cells thereby causing an increase in blood glucose levels.

Incretins are gastrointestinal hormones which cause an increase in the amount of insulin secreted by the beta cells of the pancreas after eating. This increase in insulin release occurs even before blood glucose levels are elevated. Additionally, incretins inhibit glucagon release by the pancreas. Thus, administration of incretins presents a possible mechanism for treating diabetes and other glucose regulation disorders since the incretins have the potential of both raising blood insulin levels and lowering blood glucagon levels, thereby leading to a two-pronged approach for lowering blood glucose.

Two incretins are glucagon-like peptide-1 (GLP-1), which is produced by L-cells of the intestinal mucosa, and gastric inhibitory peptide (also known as glucose-dependent insulinotropic pepide or GIP), which is produced by K-cells of the intestinal mucosa. GLP-1 and GIP are both rapidly inactivated by the enzyme dipeptidyl peptidase-4 (DPP-4). Because of this rapid inactivation, exogenous administration of incretins by injection has not been a practical approach for lowering blood glucose and, hence, treating diabetes and other glucose regulation disorders.

Embodiments of the present invention relate to methods for using stem cells for the treatment of diabetes and other glucose regulation disorders such as impaired glucose regulation disorder. In preferred embodiments, the stem cells used are desirably obtained from the bone marrow of a patient but may be obtained from any tissue in the body (e.g., skin, umbilical cord blood or tissue (e.g., Wharton's jelly), dental tissue, etc.). Embodiments of such methods are generally applicable to the treatment of any kind of diabetes, including Type I diabetes, Type II diabetes, and gestational diabetes, as well as other glucose regulation disorders. Moreover, although treatment of humans is preferred, the method may be used to treat diabetes and other glucose regulation disorders in any mammal, including monkey, cow, sheep, pig, goat, mouse, rat, dog, cat, rabbit, guinea pig, hamster and horse.

In one embodiment, the present invention is directed to a method of treating diabetes and/or other glucose regulation disorders such as impaired glucose regulation disorder. The method comprises obtaining stem cells from a patient, removing L-cells from a donor, culturing the L-cells in the presence of the stem cells under conditions such that the stem cells differentiate into stem cell-derived L-cells (SCDLC) (i.e., an autologous L-cell mimic), and introducing the mixture of SCDLC and donor L-cells into the intestinal sub-mucosa of the patient. The SCDLC will then reseed (in the submucosa of the intestine or other location) as functioning L-cells capable of secreting GLP-1, which can then cause lowering of the patient's blood glucose levels in response to the eating of a meal containing carbohydrates or fats (or other incretin stimulating compounds), and the donor L-cells will be destroyed by the patient's immune system. The cells can be introduced and placed endoscopically or by other minimally invasive means known in the gastrointestinal medical arts. The patient may be also given various medications or compounds to enhance or optimize seeding of the SCDLC cells.

In another embodiment, the present invention is directed to a method of treating diabetes or other glucose regulation disorder, with the method comprising obtaining stem cells from a patient, removing K-cells from a donor, culturing the K-cells in the presence of the stem cells under conditions such that the stem cells differentiate into stem cell-derived K-cells (SCDKC) (i.e., an autologous K-cell mimic), and introducing the mixture of SCDKC and donor K-cells into the intestinal sub-mucosa of the patient. The SCDKC will reseed as functioning K-cells capable of secreting GIP, which can then cause lowering of the patient's blood glucose level upon exposure to incretin stimulating nutrients (e.g., glucose, etc.), and the donor K-cells will be destroyed by the patient's immune system. If desired, a patient may be treated with both SCDLC and SCDKC.

In use, either of these approaches can be configured to not only lower the patient's blood glucose levels upon eating of food (e.g., carbohydrate, fatty acid, etc.) but also to lower it euglycemic concentrations after a selected time period after eating food (e.g., 2 hours or less) so as improve the patient's overall level of blood glucose regulation. In particular embodiments, either of these approaches can be used to lower the patient's blood glucose to below about 150, 120 or 100 mg/dl within two hours or less of a meal containing carbohydrates (e.g., glucose, sucrose, etc.), fatty acids or other incretin stimulating food. Further, such approaches can be configured to improve the patient's glucose regulation so as to maintain their blood glucose concentration within euglycemic levels (e.g., 150 to 80 mg/dl, or 120 to 80 mg/dl) for extended periods of time such as a day, week, month or year. Further still, the patient's long term blood glucose control can be monitored using glycosolated hemoglobin or other related analytes and monitoring means and the patient can then undergo subsequent reseedings with SCDLC and SCDKC cells as needed in improve the patient's long term glucose regulation within euglycemic levels. For example, additional reseedings can be done if the patient is found to have extended periods (e.g., weeks, etc.) of hyperglycemia.

The stem cells used in various embodiments of the invention can include pluripotent cells and multipotent cells. Examples of pluripotent cells include embryonic cells as well as reprogrammed cells discussed below. Examples of mulitpotent cells include mesenchymal stem cells also referred to as multi-potent stromal cells (both referred to as MSC's). Whatever the type, the stem cells may be from any appropriate source. For example, adult stem cells may be obtained from the patient's bone marrow, muscle, adipose tissue various connective tissue and other forms of tissue. If the patient is pregnant, stem cells such as MSC's may be obtained from umbilical cord blood and/or umbilical cord tissue (e.g., Wharton's jelly). Alternatively, amniotic stem cells can be obtained from a pregnant patient. Stem cells such as MSC's may also be collected from dental (e.g., the teeth) tissue including the developing tooth bud of for example, third molar or other molar.

Yet another source of stem cells includes reprogrammed cells (e.g., epithelial cells) which are given pluripotent capabilities. Such induced pluripotent stem cells can be made, for example, by reprogramming adult cells with protein transcription factors, such as reprogramming adult skin cells using the transcription factors Oct3/4, Sox2, c-Myc and Klf4; or the transcription factors Oct4, Sox2, Nanog and Lin28 as well as variants and other like factors.

Stem cells are typically sustained in an undifferentiated state by culture on a feeder layer of mouse embryonic fibroblasts with the inclusion of serum in the culture medium. In some embodiments, human stem cells may be maintained on a feeder layer of mouse embryonic fibroblasts with the inclusion of basis fibroblast growth factor (bFGF) in the culture medium.

For use in the methods described herein, L-cells or K-cells from a donor are typically removed by biopsy, e.g., by a needle biopsy or other biopsy device. However, any applicable method may be used, such as removal of a part of the intestine via surgery, in order to obtain L-cells or K-cells from the donor. The tissue sample containing the L-cells or K-cells is dispersed through the use of proteases or other appropriate enzymes and/or mechanical dispersal. The L-cells or K-cells may also be separated/sorted from the removed tissue sample using various cell sorting methods and equipment known in the art, for example, such as flow cytometry sorting methods including FACS sorting methods. Still other sorting methods are contemplated.

The L-cells or K-cells are typically added to the culture medium containing the stem cells, although adding the stem cells to a medium containing the L-cells or K-cells is also contemplated. The density of the stem cells and L-cells or K-cells, as well as the ratio of stem cells to L-cells or K-cells, may be adjusted for optimal results. Depending on the particular L-cell or K-cell, maintaining the cell co-culture under conditions used to maintain the stem cells may also be adequate to induce differentiation of the stem cells into stem cell-derived L-cells (SCDLC) or stem cell-derived K-cells (SCDKC). With some L-cells or K-cells, it may be desirable to remove serum or particular growth factors (e.g., bFGF) from the culture medium before differentiation of the stem cells into SCDLC or SLDKC occurs. In some cases, it may be desirable to add one or more growth factors to the culture medium to induce differentiation. These approaches can be adapted for the particular L-cells or K-cells chosen using the methods described below. Conditions found to produce differentiation can be optimized and repeated for the same or similar stem cells and donor cells (e.g., K or L cells).

Depending on culture conditions used to maintain the stem cells, they may be pluripotent, multipotent or oligopotent, with the type of stem cell being chosen so as to provide SCDLC or SCDKC with the desired characteristics. Differentiation of stem cells into SCDLC or SCDKC is typically monitored by determining the ability of the cells to produce GLP-1 or GIP, respectively, and/or the disappearance of one or more stem cell markers. For example, one can monitor the disappearance of one or more of alkaline phosphatase, alphafetoprotein (AFP), bone morphogenetic protein-4, brachyury, cluster designation 30 (CD30), cripto (TDGF-1), GATA-4 gene, GCTM-2, genesis, germ cell nuclear factor, hepatocyte nuclear factor-4 (HNF-4), nestin, neuronal cell-adhesion molecule (N-CAM), OCT4/POU5F1, Pax6, stage-specific embryonic antigen-3 (SSEA-3), stage-specific embryonic antigen-4 (SSEA-4), stem cell factor (SCF or c-Kit ligand), telomerase, TRA-1-60, TRA-1-81, or vimentin. If, for example, pluripotent stem cells are introduced into a host then, due to their pluripotent nature, it is possible that these cells will differentiate into many different types of cells, possibly causing a teratoma. Hence, it is important to insure that the SCDLC or SCDKC have lost sufficient pluripotent stem cell characteristics so as to not give rise to a teratoma in the patient.

As an additional, or alternate, criterion for determining when the stem cells have differentiated into SCDLC or SCDKC, one can monitor whether one or more cell markers of the L-cell or K-cell have appeared on the SCDLC or SCDKC. Preferably, one can monitor for the presence of one or more antigens of the L-cell or K-cell, such as one or more surface antigens.

As still another additional or alternate criterion for determining when the stem cells have differentiated into SCDLC or SCDKC, the cells can be exposed in vitro to the presence of glucose and/or a fatty acid or other incretin stimulating nutrient compound and then the cells can be monitored for minimum production of either GLP-1 or GIP (this can be determined on a batch level or individually using cell sorting methods such as FACs). In specific embodiments, only cells which produce a minimum level of GLP-1 or GIP (or other desired incretin) can then be introduced into the patient. In use, this approach provides a functional test for assuring that only those cells producing a minimum level of the desired incretin (e.g., GLP-1 or GIP) and thus capable of producing improvement in the patient's blood glucose control are introduced into the patient.

In still another related approach, the SCDLC or SCDKC cells can be conditioned in vitro to enhance the in vivo (e.g., in the patient) release of the desired incretin (e.g., GLP-1 or GIP) upon exposure to glucose, fatty acid(s) or other incretin stimulating nutrient compound. Such conditioning can include a variety of means. For example, the SCDLC or SCDKC cells can be repeatedly exposed in vitro to selected concentrations of glucose and/or a fatty acid or incretin stimulating compound. The cells can be monitored for production of either GLP-1 or GIP or other desired incretin and the concentrations of glucose, fatty acid(s) or other incretin stimulatory nutrient compound can be titrated (up or down) on each round of exposure to enhance the release of the desired incretin. Experiments can be done to determine the optimal concentration of glucose, fatty acid, etc., for enhancing the release of the desired incretin for a particular combination of patient stem cells and donor cells (e.g., L-cell, K-cells). In one variant of this approach, conditioning can be done when the patient's stem cells and donor cells are being co-cultured to differentiate the stem cells into the desired SCDLC or SCDKC cells. Using such an approach, the stem cells are exposed to cell signaling peptides or other compounds secreted by the donor cells to stimulate production of the desired incretin. In this way, the stem cells are conditioned to produce the desired incretin in a like manner to the donor cells. Repeated cycles of conditioning can be performed using a particular regimen of glucose/fatty acid concentrations. As an alternative or addition to this approach, during one or more exposures to incretin stimulating compound, or co-culturing with the donor cells, the stem cells can be exposed to a particular regimen of electrical stimulation (e.g., voltages in the range of about 1 to 10 mv, or 10 to 100 mv, with smaller and larger ranges contemplated). Electrical stimulation can also be done as a separate conditioning step, before or after other conditioning steps (e.g., co-culturing, exposure to incretin stimulating compounds, etc.). The electrical stimulation can be done using various voltage sources including programmable voltage sources known in the art. Use of the latter can be configured to reproduce a particular voltage conditioning regimen for the production of multiple batches of SCDLC's or SLDKC's or other like cells.

Conclusion

The foregoing description of various embodiments of the invention has been presented for purposes of illustration and description. It is not intended to limit the invention to the precise forms disclosed. Many modifications, variations and refinements will be apparent to practitioners skilled in the art. For example, embodiments of the invention can be readily adapted for stem cells not disclosed herein, or other cells having stem cell like properties. Additionally, embodiments of the invention can be adapted for patients having disorders other than blood glucose regulation disorders. Further, embodiments of the invention can be readily adapted for pediatric and even neonatal applications.

Elements, characteristics, or acts from one embodiment can be readily recombined or substituted with one or more elements, characteristics or acts from other embodiments to form numerous additional embodiments within the scope of the invention. Moreover, elements or acts that are shown or described as being combined with other elements or acts, can, in various embodiments, exist as standalone elements or acts. Hence, the scope of the present invention is not limited to the specifics of the described embodiments, but is instead limited solely by the appended claims.

What is claimed is:

1. A method for treating diabetes, the method comprising:
   obtaining L-cells from a donor;
   obtaining stem cells from a patient;
   culturing the L-cells in the presence of the stem cells under conditions such that the stem cells differentiate into stem cell-derived L-cells (SCDLC); and
   introducing an amount of the SCDLC into the patient sufficient to cause a lowering of the patient's blood glucose level after the ingestion of food.

2. The method of claim 1, wherein the method is used for treating Type I diabetes.

3. The method of claim 1, wherein the method is used for treating Type II diabetes.

4. The method of claim 1, wherein the stem cells are obtained from adult bone marrow.

5. The method of claim 1, wherein the stem cells are obtained from umbilical cord blood or umbilical cord tissue.

6. The method of claim 1, wherein the stem cells are obtained from amniotic fluid.

7. The method of claim 1, wherein the stem cells are obtained from dental tissue.

8. The method of claim 1, wherein the stem cells are induced pluripotent stem cells.

9. The method of claim 1, wherein the stem cells are pluripotent stem cells.

10. The method of claim 1, wherein the stem cells are multipotent stem cells.

11. The method of claim 1, wherein the stem cells are mesenchymal stem cells.

12. The method of claim 1, wherein the stem cells are oligopotent stem cells.

13. The method of claim 1, wherein the SCDLC do not express a pluripotent stem cell marker.

14. The method of claim 13, wherein the SCDLC do not express the cell surface antigen SSEA3.

15. The method of claim 13, wherein the SCDLC do not express the cell surface antigen SSEA4.

16. The method of claim 13, wherein the SCDLC do not express the cell surface antigen Tra-1-60.

17. The method of claim 13, wherein the SCDLC do not express the cell surface antigen Tra-1-81.

18. The method of claim 1, wherein the SCDLC do not express a multipotent stem cell marker.

19. The method of claim 1, wherein the SCDLC do not express an oligopotent stem cell marker.

20. The method of claim 1, wherein the SCDLC express at least one cell surface antigen mimic of a cell surface antigen of the L-cells obtained from the donor.

21. The method of claim 1, wherein the L-cells are obtained using a biopsy device.

22. The method of claim 1, wherein the patient's glucose level is lowered below about 150 mg/dl within two hours after ingestion of food.

23. The method of claim 1, wherein the patient's glucose level is lowered below about 120 mg/dl within two hours after ingestion of food.

24. The method of claim 1, wherein the patient's glucose level is lowered below about 100 mg/dl within two hours after ingestion of food.

25. The method of claim 1, wherein the food comprises a carbohydrate or a fat.

26. A method for treating diabetes, the method comprising:
    obtaining L-cells from a donor;
    obtaining stem cells from a patient;
    culturing the L-cells in the presence of the stem cells under conditions such that the stem cells differentiate into stem cell-derived L-cells (SCDLC); and
    introducing an amount of the SCDLC into the patient sufficient to maintain the patient's blood glucose levels within euglycemic levels for an extended period.

27. The method of claim 26, wherein the extended period is up to about a day, a week, a month, or a year.

28. The method of claim 26, further comprising:
    sorting the SCDLC in vitro for those cells producing a minimum level of GLP-1 in response to the presence of glucose or a fatty acid, wherein only those SCDLC which produce the minimum level of GLP-1 are introduced into the patient.

29. The method of claim 26, further comprising:
    conditioning the SCDLC in vitro to enhance release of GLP-1 in response to the presence of at least one of glucose or a fatty acid.

* * * * *